United States Patent [19]

Danner et al.

[11] Patent Number: 4,871,701

[45] Date of Patent: Oct. 3, 1989

[54] ALKALI-FREE PREPARATION OF LARGE PENTASIL CRYSTALS AS COATED CATALYSTS AND FULLY CRYSTALLINE CATALYSTS

[75] Inventors: Alfred Danner, Bensheim; Ulaich Mueller, Schlangenbad; Klaus Unger, Seeheim; Wolfgang Hoelderich, Frankenthal, all of Fed. Rep. of Germany

[73] Assignee: BASF Aktiengesellschaft, Ludwigshafen, Fed. Rep. of Germany

[21] Appl. No.: 235,620

[22] Filed: Aug. 24, 1988

[30] Foreign Application Priority Data

Aug. 26, 1987 [DE] Fed. Rep. of Germany ....... 3728451

[51] Int. Cl.$^4$ .............................................. B01J 29/28
[52] U.S. Cl. ......................................... 502/62; 502/71
[58] Field of Search ............................ 502/62, 64, 71; 423/328 T

[56] References Cited

U.S. PATENT DOCUMENTS

| | | | |
|---|---|---|---|
| 3,244,643 | 4/1966 | Schwartz | 502/64 |
| 3,359,068 | 12/1967 | Michalko | 502/60 |
| 3,445,184 | 5/1969 | Whittemore, Jr. | 23/112 |
| 3,468,815 | 9/1969 | Cole et al. | 502/64 |
| 3,523,092 | 8/1970 | Kearby | 502/64 |
| 3,650,687 | 3/1972 | McDaniel et al. | 502/60 |
| 3,702,886 | 11/1972 | Argauer et al. | 423/328 |
| 4,205,503 | 5/1980 | Rollman et al. | 423/329 |
| 4,404,175 | 9/1983 | Marosi et al. | 423/329 |
| 4,420,419 | 12/1983 | Ogawa et al. | 502/68 |
| 4,424,144 | 1/1984 | Pryor et al. | 502/68 |
| 4,551,321 | 11/1985 | Marosi et al. | 423/328 T |
| 4,563,435 | 1/1986 | Chu et al. | 502/71 |
| 4,582,815 | 4/1986 | Bowes | 502/64 |
| 4,594,332 | 6/1986 | Hoelderich et al. | 502/64 |

FOREIGN PATENT DOCUMENTS 0014546 8/1980 European Pat. Off. .
0178687 4/1986 European Pat. Off. .

OTHER PUBLICATIONS

Y. Murakami et al. Proceedings of the 7th International Zeolite Conference Tokyo, Aug. 17–22, 1986 pp. 121–128, (1986).

Primary Examiner—Carl F. Dees
Attorney, Agent, or Firm—Keil & Weinkauf

[57] ABSTRACT

Pentasil coated catalysts and fully crystalline catalysts in which the individual pentasil crystals are larger than 5 μm are prepared by hydrothermal treatment of $SiO_2$ by a process in which the $SiO_2$ moldings are subjected to a hydrothermal treatment at from 140° to 220° C. in an alkali-free mixture of water, an amine and/or a tetraalkylammonium compound, with or without ammonia. The aluminum component for the preparation of an aluminosilicate zeolite can be kneaded into the $SiO_2$ moldings or fed in via the liquid phase during the hydrothermal treatment. The tetraalkylammonium compound used can be a tetra-n-propyl-ammonium salt or hydroxide.

4 Claims, No Drawings

ALKALI-FREE PREPARATION OF LARGE PENTASIL CRYSTALS AS COATED CATALYSTS AND FULLY CRYSTALLINE CATALYSTS

In the preparation of moldings from zeolite powder, the use of binders is indispensable. Suitable binders are organic compounds, such as ethylcellulose (U.S. Pat. No. 4,333,768) and polysilicates (German Patent No. 3,231,498), as well as inorganic compounds, such as alumina (U.S. Pat. No. 4,563,435), silica gel (European Patent No. 167,324) and clays (German Patent No. 3,208,672).

Hydrothermal reactions of premolded carriers of clay-containing materials, some with appropriate addition of zeolites, to give zeolite moldings are known, for example, for mordenite (U.S. Pat. No. 3,445,184), faujasite (German Patent No. 1,567,894) and zeolite A (German Patent No. 3,242,126), the product in each case being pellets which consist exclusively of the corresponding zeolites. It is also known (European Patent No. 201,264) that zeolites of type ZSM-5 are prepared in this manner, the use of seed crystals being a precondition and the conversion to ZSM-5 taking place only with poor yields. Zeolites of type ZSM-5 are described in U.S. Pat. No. 3,702,886, as is their preparation in powder form.

We have found that, in the alkali-free preparation of large pentasil crystals as coated catalysts and fully crystalline catalysts, in which the individual pentasil crystals are larger than 5 μm, by hydrothermal treatment of $SiO_2$, good results are obtained if $SiO_2$ moldings are subjected to a hydrothermal treatment at from 140° to 220° C. in an alkali-free mixture of water, an amine and/or a tetraalkylammonium compound, with or without ammonia.

In the novel preparation of pentasil coated catalysts and fully crystalline catalysts by hydrothermal reaction of $SiO_2$ pellets in the form of spheres or extrudates, the starting materials used are synthesis mixtures which do not contain any alkali metal ions. The aluminum component can either be added to the reaction solution as a soluble aluminum compound, for example as an aluminum salt, aluminum alcoholate or aluminum hydroxide, or can be incorporated as a solid component during the preparation of the $SiO_2$ molding itself, for example kneaded in as alumina or pseudoboehmite.

Suitable $SiO_2$ sources for the preparation of the moldings are all conventional $SiO_2$-containing materials, for example silica gel or pyrogenic silica or finely divided silica. The $SiO_2/Al_2O_3$ ratio can be varied from α to 8:1. The ratio of from 100:1 to 30 : 1 is preferred.

Using the novel process, pentasil crystals whose longitudinal axes are longer than 5 μm are formed in the moldings. By adjusting the process conditions, for example duration of synthesis and $H_2O/SiO_2$ ratio, it is also possible to obtain sizes of from 50 to 200 μm. Crystals of this size possess high shape selectivity. If the aluminum component is incorporated during preparation of the moldings, it may be incorporated in the form of a powder or in the form of a gel peptized with a mineral acid, for example nitric acid, and the amount of acid can be varied from 0.016 to 0.227 g/g of $Al_2O_3$. When mineral acid is added, the crystal size decreases.

Ammonia, amines and water may be used as binding liquids. Dilute ammonia solution is preferably used. The proportion of ammonia is from 0 to 32%, preferably 2.5%. The amount of binder liquid can be from 125 to 170, preferably from 150 to 160, g/100 g of $SiO_2$. Molding can be carried out using a known process, for example extrusion. The resulting moldings can be reacted in the dry state as well as in the calcined or partially sintered state.

To convert the amorphous moldings, which have been dried at about 100°–140° C. and/or calcined at 500°–600° C., to a pentasil zeolite, the said moldings are impregnated with an aqueous solution of an amine or a tetraalkylammonium compound, preferably a tetra-n-proplylammonium salt or hydroxide, and, if required $NH_3$ dissolved in water, and are subjected to a hydrothermal reaction in an autoclave at from 140° to 220° C., preferably from 160 to 200° C., for a reaction time of from 1 to 30, preferably from 1 to 7, days. The aluminum is already present in the moldings in the form of pseudoboehmite.

TABLE 1

Reaction conditions for the hydrothermal preparation of pentasil moldings

|  | General | Preferred |
|---|---|---|
| $SiO_2/Al_2O_3$ | 8–∞ | 30–100 |
| $H_2O/SiO_2$ | 5–100 | 10–40 |
| $OH/SiO_2$ | 0.01–6 | 0.13–4 |
| $R/SiO_2$ | 0.01–0.3 | 0.04–0.17 |
| Reaction time | 1–30 days | 1–7 days |
| Reaction temp. | 140 to 220° C. | 160 to 200° C. |

R = amine, tetraalkylammonium compound

This procedure gives moldings which are fully crystalline and have a ZSM-5 content of up to 95% and crystal sizes of up to 100 μm.

If, for example, the pure $SiO_2$ pellets dried at about 120° C. are taken and the aluminum is added to the synthesis solution described above in the form of a soluble component, moldings having a core of 100% of ZSM-5 and a coating of amorphous $SiO_2$ are obtained. The reaction conditions are shown in Table 1.

If partially sintered $SiO_2$ moldings (eg. commercial $SiO_2$ carriers) are used as a starting material in the process, a coating of ZSM-5 crystals which consists of only one or two crystal layers is formed.

Whether a fully crystalline molding is formed or only a coating depends to a critical extent on whether the initial moldings have a broad pore size distribution with one or more broad maxima at about 60 nm pore diameter (fully crystalline) or a narrow distribution with a sharp maximum at about 8 nm pore diameter (coating).

By calcination at from 450° to 600° C., preferably 550° C., for from 4 to 30, preferably 24, hours, the moldings are directly converted into the catalytically active H form. The pentasil moldings possess high shape selectivity. In the test reaction for the shape selectivity of the synthesized catalysts, the disproportionation of ethylbenzene (Karge, Journal of Catalysis 82 (1983), 236), the isomer mixture of the diethylbenzenes is found to contain up to 96% of para-diethylbenzene.

The crystalline pentasil fraction in the moldings, referred to below as crystallinity, is determined by treating the moldings with about 30% strength NaOH at room temperature for 5 days. The amorphous fractions are dissolved away in this process. The size of the pentasil crystals is determined under the optical microscope and by means of the scanning electron microscope.

The novel catalysts are suitable for hydrocarbon conversions, for example the conversion of methanol and/or dimethyl ether to hydrocarbons, the conversion of epoxides to aldehydes and of aldehydes to ketones, skeletal and valency isomerizations of hydrocarbons and the amination of olefins, the hydroformylation of olefins, dehydration reactions with alcohols, aldehydes and amides, acetal cleavage reactions and carbonylation and decarbonylation reactions, as carriers for hydrogenation and dehydrogenation catalysts and for further organic syntheses (W. Hölderich, Pure and Appl. Chem. 58, 10 (1986), 1393). The catalysts according to the invention are particularly suitable for reactions in a fluidized bed.

EXAMPLES 1 to 9

In Examples 1 to 6, fully crystalline pentasil catalysts are prepared from $SiO_2$ moldings into which the aluminum component has been kneaded.

EXAMPLE 1

6.6 g of pseudoboehmite (AlOOH, 12% loss on drying at 120° C.) are dispersed in 200 g of 2.5% strength ammonia solution, the dispersion is transferred to a kneader and 120 g of pyrogenic silica are kneaded in over 22 minutes. The resulting paste is extruded, and dried at 120° C. for 24 hours in a drying oven.

12.6 g of the dry extrudates are introduced together with a solution of 7.1 g of tetra-n-propylammonium bromide, 21.4 g of $H_2O$ and 18.1 g of 25% strength ammonia solution into an autoclave and allowed to react for 5 days at 185° C.

To determine the crystallinity, some of the resulting moldings are dried and then treated with about 30% strength NaOH, the amorphous fractions being dissolved away. Another portion is converted into the catalytically active H form by calcination for 24 hours at 550° C., and its selectivity is investigated for the ethylbenzene disporportionation reaction. In this test, the reaction temperature was always 250° C. and the saturator temperature 20° C. The space velocity is adjusted so that a conversion of 2% is obtained.

The resulting extrudates consist of 89% of $NH_4$-ZSM-5. The isomer mixture of the 3 diethylbenzenes formed in the catalytic test at 2% conversion consist of 95.9% of the para-isomer and 4.1% of the meta-isomer.

EXAMPLE 2

The moldings prepared in Example 1 are treated hydrothermally for 1 day under otherwise identical conditions. Thereafter, they consist of 50% of $NH_4$-ZSM-5. The selectivity test indicates 94.8% of para-diethylbenzene.

EXAMPLE 3

The extrudates prepared in Example 1 are calcined for 4 hours at 550° C. before the hydrothermal treatment. Under otherwise identical conditions, extrudates containing 62% of $NH_4$-ZSM-5 are formed. The selectivity with respect to para-diethylbenzene is 94.7%.

The next three Examples serve to illustrate the effect of the acidic pretreatment of the aluminum component.

EXAMPLE 4

3.3 g of pseudoboehmite (AlOOH, 12% loss on drying at 120° C.) are dispersed in 150 g of 1% strength ammonia solution, the solution is transferred to a kneader and 120 g of pyrogenic silica are kneaded in over 22 minutes. The paste is extruded, and 12.3 g of the extrudates dried as described under 1 are subjected to a hydrothermal reaction as described in Example 1.

The resulting moldings consist of 83% of $NH_4$-ZSM-5 and exhibit a para selectivity of 44.3%.

EXAMPLE 5

A gel consisting of 3.3 g of pseudoboehmite (AlOOH, 12% loss on drying at 120° C.) and 4.4 g of 1% strength nitric acid is dispersed in 145.4 g of ammonia solution, the dispersion is kneaded with 120 g of pyrogenic silica the product is extruded and the extrudates are further treated as described in Example 4 but are subjected to the hydrothermal reaction for only 2 days. The resulting moldings have a crystallinity of 38% and para selectivity of 54.6% for diethylbenzene.

EXAMPLE 6

3.3 g of pseudoboehmite (AlOOH, 12% loss on drying at 120° C.) are dispersed in 150 g of 0.5 strength nitric acid and the dispersion is kneaded with 120 g of pyrogenic silica. The further treatment is carried out as described in Example 4. The resulting moldings have a crystallinity of 77% and exhibit a para selectivity of 93.5% for diethylbenzene.

In the abovementioned Examples, the crystals are homogeneously distributed over the entire cross-section of the moldings. The next Examples describe the results for the addition of the aluminum component to the synthesis solution.

EXAMPLE 7

120 g of pyrogenic silica are kneaded into 200 g of 2.5% strength ammonia solution and the mixture is then extruded. A solution of 3.77 g of tetra-n-propylammonium bromide, 47.7 g of $H_2O$, 23 g of 32% strength ammonia solution and 0.732 g of aluminum triisopropylate is added to 6.4 g of the extrudates dried at 120° C. for 24 hours, and the mixture is reacted in an autoclave for 4 days at 185° C. The resulting moldings have a core which consists of 100% of $NH_4$-ZSM-5 and a shell which consists of amorphous $SiO_2$ and is detached on calcination. The catalytic test of the moldings activated as in Example 1 indicate a content of 94.3% of para-diethylbenzene in the isomer mixture.

EXAMPLE 8

A solution of 59.4 g of tetra-n-propylammonium bromide, 255 g of $H_2O$ and 160 g of 25% strength ammonia solution is added to 100 g of commercial $SiO_2$ spheres having a diameter of 3 to 5 mm, and the mixture is reacted in an autoclave for 5 days at 185° C. The resulting moldings consist of spheres of amorphous $SiO_2$, on which a layer of $NH_4$-ZSM-5 has grown. No catalytic activity is detectable for this ZSM-5 prepared in the absence of aluminum.

EXAMPLE 9

A solution of 11.8 g of tetra-n-propylammonium bromide, 60.8 g of $H_2O$, 29.6 g of 25% strength ammonia solution and 0.28 g of pseudoboehmite (AlOOH, 12% loss on drying at 120° C.) is added to 20 g of commercial $SiO_2$ spheres (diameter 1 mm, Kali-Chemie), and the mixture is reacted in an autoclave for 5 days at 185° C. Moldings of amorphous $SiO_2$ on which a layer of $NH_4$-ZSM-5 has grown are formed. After the product has been calcined for 24 hours at 550° C., the para selectivity is 94.1%.

Table 2 summarizes the properties of the moldings.

TABLE 2

| Example No. | Crystallinity [%] | Size of the pentasil crystals [μm] | Para selectivity in the EBD test* [%] |
|---|---|---|---|
| 1 | 89 | 90–100 | 95.9 |
| 2 | 50 | 50–60 | 94.8 |
| 3 | 62 | 95–105 | 94.7 |
| 4 | 83 | 7–12 | 44.3 |
| 5 | 38 | 6–9 | 54.6 |
| 6 | 77 | 7–12 | 93.5 |
| 7 | 100 (in core) | 90–100 | 94.3 |
| 8 | 100 (in coating) | 50–60 | — |
| 9 | 100 (in coating) | 40–50 | 94.1 |

*EBD = ethylbenzene disproportionation

We claim:

1. A process for the alkali-free preparation of large pentasil crystals as coated catalysts and fully crystalline catalysts, in which the individual pentasil crystals are larger than 5 μm, by hydrothermal treatment of $SiO_2$, wherein the $SiO_2$ moldings are subjected to a hydrothermal treatment at from 140° to 220° C. in an alkali-free mixture of water, an amine and/or a tetraalyklammonium compound, with or without ammonia.

2. A process as claimed in claim 1, wherein the aluminum component for the preparation of an aluminosilicate zeolite is kneaded into the $SiO_2$ moldings.

3. A process as claimed in claim 1, wherein the aluminum component for the preparation of an aluminosilicate zeolite is fed in via the liquid phase during the hydrothermal treatment.

4. A process as claimed in claim 1, wherein the tetraalkylammonium compound used is a tetra-n-propylammonium salt or hydroxide.

* * * * *